US009649134B2

(12) United States Patent
Hannen

(10) Patent No.: US 9,649,134 B2
(45) Date of Patent: May 16, 2017

(54) UNIPLANAR SCREW ASSEMBLY AND METHODS OF USE

(71) Applicant: Alphatec Spine, Inc., Carlsbad, CA (US)

(72) Inventor: Matthew Hannen, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 385 days.

(21) Appl. No.: 14/250,685

(22) Filed: Apr. 11, 2014

(65) Prior Publication Data

US 2014/0343617 A1 Nov. 20, 2014

Related U.S. Application Data

(60) Provisional application No. 61/811,220, filed on Apr. 12, 2013.

(51) Int. Cl.
*A61B 17/70* (2006.01)
*A61B 17/86* (2006.01)

(52) U.S. Cl.
CPC ...... *A61B 17/7038* (2013.01); *A61B 17/7032* (2013.01); *A61B 17/8605* (2013.01)

(58) Field of Classification Search
CPC . A61B 17/70; A61B 17/7032; A61B 17/7034; A61B 17/7035; A61B 17/7038; A61B 17/80; A61B 17/8033; A61B 17/8047; A61B 17/86; A61B 17/8605; A61B 17/861; A61B 17/8615; A61B 17/862
USPC ............................................. 606/305–308
See application file for complete search history.

(56) References Cited

U.S. PATENT DOCUMENTS

| | | | |
|---|---|---|---|
| 5,989,254 A | 11/1999 | Katz | |
| 6,692,500 B2 | 2/2004 | Reed | |
| 6,800,078 B2 | 10/2004 | Reed | |
| 6,800,079 B2 | 10/2004 | Reed | |
| 7,087,057 B2 * | 8/2006 | Konieczynski | .... A61B 17/7032 606/278 |
| 7,635,380 B2 * | 12/2009 | Zucherman | ........ A61B 17/7035 606/267 |
| 7,749,258 B2 | 7/2010 | Biedermann et al. | |
| 7,766,944 B2 | 8/2010 | Metz-Stavenhagen | |
| 7,951,172 B2 | 5/2011 | Chao et al. | |
| 7,951,179 B2 * | 5/2011 | Matityahu | .......... A61B 17/7059 606/300 |

(Continued)

FOREIGN PATENT DOCUMENTS

| | | |
|---|---|---|
| EP | 2457527 | 5/2012 |
| EP | 2559391 | 2/2013 |

*Primary Examiner* — Christian Sevilla
*Assistant Examiner* — Eric S Gibson
(74) *Attorney, Agent, or Firm* — Dinsmore & Shohl LLP

(57) ABSTRACT

The screw assembly includes a screw, an insert, and a body member. The screw includes a longitudinal axis and a proximal end with a head portion and a distal end with a threaded portion. The insert operably couples with the head portion and is configured to rotate relative to the head portion about the longitudinal axis. The body member operably couples with the insert and is configured to pivot relative to the insert in a single plane parallel to the longitudinal axis. In other features, the body member operably couples with the insert and is configured to pivot relative to the insert about a transverse axis normal to a plane parallel to the longitudinal axis.

11 Claims, 14 Drawing Sheets

(56) References Cited

U.S. PATENT DOCUMENTS

| | | | |
|---|---|---|---|
| 8,012,186 B2 | 9/2011 | Pham et al. | |
| 8,038,701 B2* | 10/2011 | Rock | A61B 17/7032 606/266 |
| 8,298,275 B2 | 10/2012 | Rezach | |
| 8,361,126 B2* | 1/2013 | Perrow | A61B 17/8047 606/287 |
| 8,398,683 B2 | 3/2013 | Berrevoets et al. | |
| 8,419,778 B2 | 4/2013 | Barry | |
| 8,430,917 B2 | 4/2013 | Rezach | |
| 8,449,578 B2* | 5/2013 | Keiser | A61B 17/7032 606/264 |
| 8,470,009 B1* | 6/2013 | Rezach | A61B 17/7038 606/300 |
| 8,623,019 B2* | 1/2014 | Perrow | A61B 17/1671 606/279 |
| 8,628,558 B2* | 1/2014 | Harvey | A61B 17/7049 606/267 |
| 8,986,349 B1* | 3/2015 | German | A61B 17/7068 606/279 |
| 9,044,272 B2* | 6/2015 | Shaffrey | A61B 17/7032 606/264 |
| 2007/0088357 A1* | 4/2007 | Johnson | A61B 17/7037 606/86 A |
| 2007/0162016 A1* | 7/2007 | Matityahu | A61B 17/7059 606/281 |
| 2008/0154315 A1 | 6/2008 | Jackson | |
| 2008/0161859 A1* | 7/2008 | Nilsson | A61B 17/7032 606/266 |
| 2008/0177260 A1* | 7/2008 | McKinley | A61B 17/7038 606/60 |
| 2008/0177321 A1* | 7/2008 | Drewry | A61B 17/7032 606/266 |
| 2008/0249570 A1* | 10/2008 | Carson | A61B 17/7038 606/264 |
| 2008/0306550 A1* | 12/2008 | Matityahu | A61B 17/1728 606/290 |
| 2009/0012571 A1* | 1/2009 | Perrow | A61B 17/1671 606/280 |
| 2009/0062862 A1* | 3/2009 | Perrow | A61B 17/8047 606/280 |
| 2009/0069852 A1* | 3/2009 | Farris | A61B 17/7038 606/301 |
| 2009/0076552 A1* | 3/2009 | Tornier | A61B 17/7038 606/264 |
| 2009/0105769 A1* | 4/2009 | Rock | A61B 17/7032 606/308 |
| 2010/0145394 A1* | 6/2010 | Harvey | A61B 17/7049 606/302 |
| 2010/0204735 A1* | 8/2010 | Gephart | A61B 17/7032 606/264 |
| 2011/0009911 A1* | 1/2011 | Hammill, Sr. | A61B 17/7037 606/308 |
| 2011/0106174 A1* | 5/2011 | Rezach | A61B 17/7032 606/305 |
| 2011/0112578 A1* | 5/2011 | Keiser | A61B 17/7032 606/264 |
| 2011/0178559 A1 | 7/2011 | Barry | |
| 2011/0196431 A1 | 8/2011 | Chao et al. | |
| 2012/0016425 A1* | 1/2012 | Shaffrey | A61B 17/7032 606/305 |
| 2012/0046701 A1* | 2/2012 | Gennari | A61B 17/7076 606/308 |
| 2012/0245641 A1* | 9/2012 | Mekhail | A61B 17/8047 606/279 |
| 2013/0226243 A1* | 8/2013 | Kraus | A61B 17/7032 606/264 |
| 2014/0236235 A1* | 8/2014 | Jackson | A61B 17/7037 606/267 |
| 2014/0343617 A1* | 11/2014 | Hannen | A61B 17/8605 606/306 |
| 2015/0223846 A1* | 8/2015 | Shaffrey | A61B 17/7032 606/270 |
| 2015/0282844 A1* | 10/2015 | Vedula | A61B 17/7032 606/305 |

\* cited by examiner

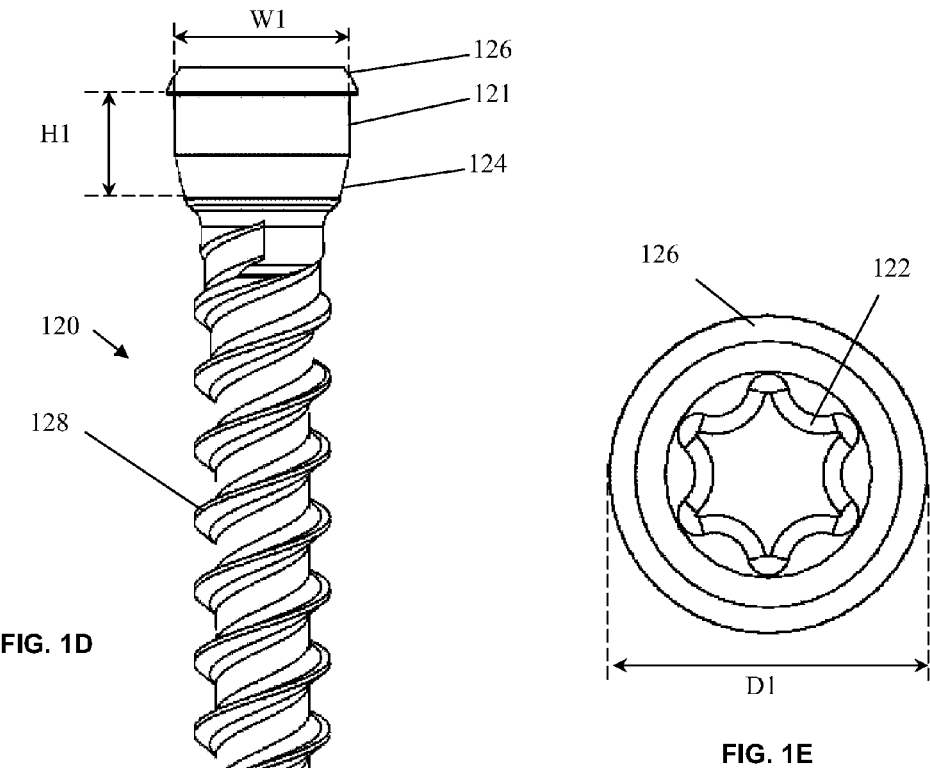
FIG. 1D
FIG. 1E
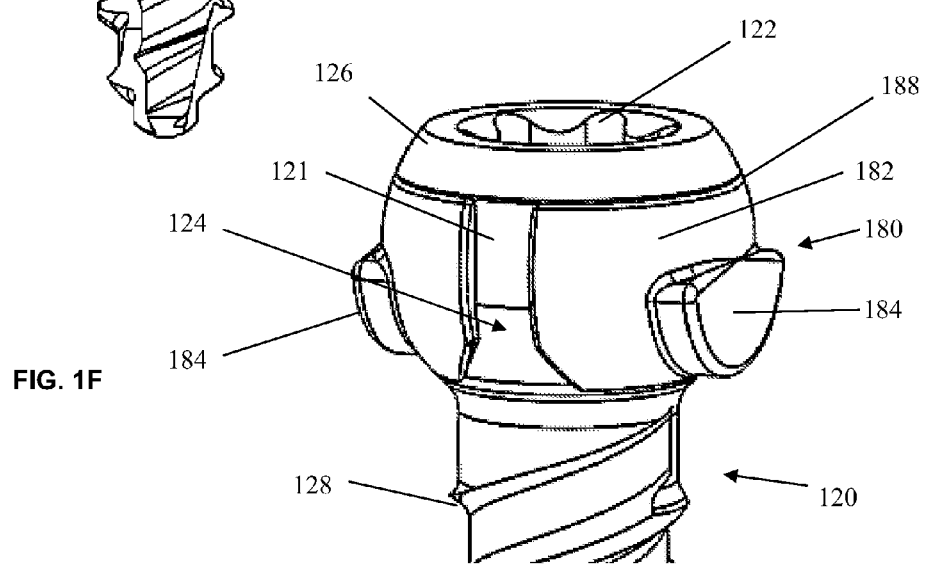
FIG. 1F

FIG. 4C
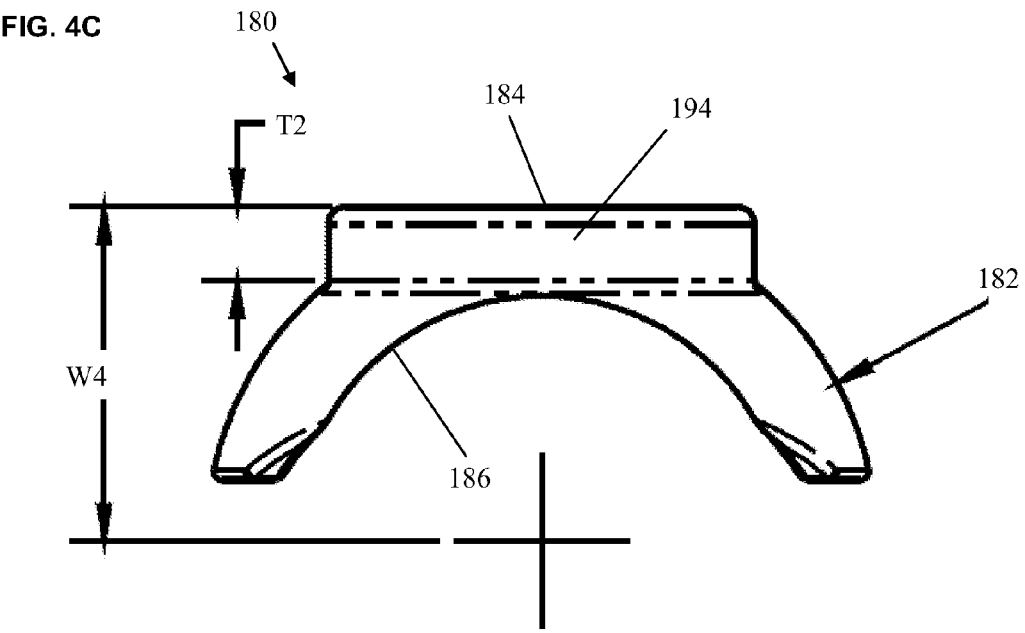
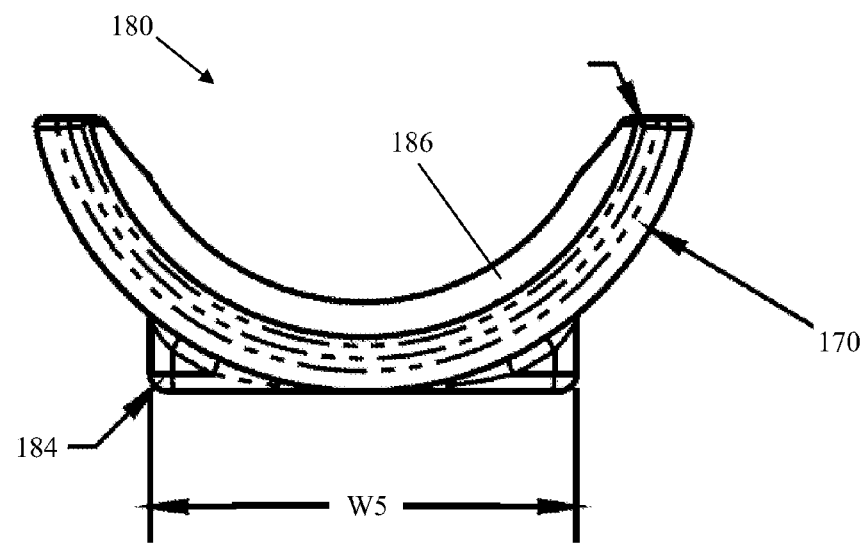
FIG. 4D

UNIPLANAR SCREW ASSEMBLY AND METHODS OF USE

CROSS-REFERENCE TO RELATED APPLICATIONS

The present application claims priority to U.S. Provisional Application Ser. No. 61/811,220 entitled "Uniplanar Screw Assembly and Methods of Use" which was filed on Apr. 12, 2013 and is incorporated herein by reference in its entirety.

FIELD

The present invention relates generally to an apparatus for internal fixation of the spine.

BACKGROUND

Certain spinal conditions, including a fracture of a vertebra and a herniated disc, indicate treatment by spinal immobilization. Several methods of spinal joint immobilization are known, including surgical fusion and the attachment of pins and bone plates to the affected vertebras. One known device is a bone interface anchor inserted into at least two spaced-apart vertebras, with a stabilization rod interconnecting the two or more anchors to stabilize the vertebras spanned by the anchors.

Specifically, a bone screw is received within a socket formed in the anchor. The anchor further includes a channel, extending perpendicular to the longitudinal axis of the bone screw, for receiving the stabilization rod. The anchor further comprises a threaded portion above the channel. After the bone screw and anchor have been inserted into the bone material, the rod is placed within the channel and a nut is mated with the external threads of the anchor. The nut applies a compressive force between the rod and the screw head to firmly fix the rod between the spanned vertebras and thus stabilize the spinal vertebrae.

During surgical implantation of these prior art stabilization systems, the surgical site is crowded with tissue masses, sponges and other surgical implements that obstruct access to the anchor threads. Given the difficult access, it is possible for the surgeon to cross-thread the nut with the threads of the anchor after the fixation rod is in place. If the threads of the anchor are cross-threaded, the cross-threaded coupling must be removed and replaced before the surgery can proceed. In addition, the threaded fastener (e.g., the nut) is frequently removed and then reinstalled as the surgeon makes progressive bends to contour the fixation rod. This increases the surgery with each on-off iteration and further increases the chances of cross-threading.

Another problem associated with threaded attachments is the torque exerted on the anchor during the tightening of the threaded fastener about the upper end portion of the fixation device. This torque can inadvertently introduce stress points along the rod, bend the rod, or even loosen the threaded engagement of the anchor in the bone. The elimination of the conventional threaded attachments in the fixation device of the present invention also obviates these problems associated with applying torque.

The angle at which the anchor screws extend from the vertebra pedicle is dictated by the spinal curvature, the orientation of individual vertebra within the spine, and the surgeon's placement of the screw within the pedicle. For example, there is considerable spinal curvature in the region of the S1-L5 vertebra junction and the angle between the longitudinal axis of the screws and the vertebra in that region vary over a wide range. Also, it may be necessary to displace one or more of the anchors from the spin midline to effectuate maximum spinal stabilization. Thus, the rod-receiving channels are typically not collinear or coplanar and, the rod must be shaped or contoured by the surgeon during the implantation procedure to fit within the channels along the spinal column. The prior art systems allow the coupling unit to pivot with respect to the screw over a range of about +/−0.20° to +/−0.3°, providing some margin for the surgeon to place the rod within the channel.

Current uniplanar screws contain flat features on the screw shank that are engaged by mating flat features on the bushing/load ring component to prevent motion in one plane. Other designs have features on the shank itself that engage the screw body to only allow motion in one plane. None of the existing designs allow the shank to rotate independently of the screw body. Other devices lock rotation of the shank to the body which limits the thread forms that are preferred for pedicle screws. Thus, the present invention addresses these problems as well as others.

SUMMARY OF THE INVENTION

Provided herein are systems and methods for a screw assembly.

The screw assembly includes a screw, an insert, and a body member. The screw includes a longitudinal axis and a proximal end with a head portion and a distal end with a threaded portion. The insert operably couples with the head portion and is configured to rotate relative to the head portion about the longitudinal axis. The body member operably couples with the insert and is configured to pivot relative to the insert in a single plane parallel to the longitudinal axis. In other features, the body member operably couples with the insert and is configured to pivot relative to the insert about a transverse axis normal to a plane parallel to the longitudinal axis.

In other features, the insert further includes at least a partially curved interior surface configured to engage a curved lateral surface of the head portion. The insert permits 360 rotation of the body member relative to the head portion about the longitudinal axis. The insert further includes extensions projecting radially away from the longitudinal axis and into recessed portions of the body member.

In still other features, the extensions include two extensions that are diametrically opposed about the insert. The extensions include proximal surfaces that angle away from a plane that is normal to the longitudinal axis by a predetermined angle and are configured to limit pivoting of the body member to a predetermined pivot angle. The extensions include distal surfaces that are curved and configured to permit pivoting of the body member.

In yet other features, the screw assembly includes a bushing disposed between the body member and the head portion.

In yet other features, the screw assembly includes a screw, an insert, and a screw. The screw has a longitudinal axis and a proximal end with a head portion having a curved circumferential surface and a distal end with a threaded portion. The insert includes at least a partially curved interior surface that engages the curved circumferential channel to rotate relative to the head portion about the longitudinal axis. The insert includes extensions projecting radially away from the longitudinal axis. The body member includes recessed portions that receive the extensions to pivot the body member relative to the insert about an axis in a plane normal to the longitudinal axis.

In other features, the insert further includes two diametrically opposed extensions projecting radially away from the longitudinal axis and into recessed portions of the body member. The head portion includes a cap having a diameter greater than a diameter of a proximal opening of the insert to prevent passage of the head portion distally through the insert and body member. The extensions include proximal surfaces that angle away from a plane that is normal to the longitudinal axis by a predetermined angle and are configured to limit pivoting of the body member to a predetermined pivot angle. The distal surfaces are curved and configured to permit pivoting of the body member.

BRIEF DESCRIPTION OF THE DRAWINGS

In the accompanying figures, like elements are identified by like reference numerals among the several preferred embodiments of the present invention.

FIG. 1D is a side view of the screw, according to one embodiment.

FIG. 1E is a top view of the screw, according to one embodiment.

FIG. 1F is a perspective view of the screw head portion operably coupled with the insert.

FIG. 4C is a top view of the insert, according to one embodiment.

FIG. 4D is bottom view of the insert, according to one embodiment.

DETAILED DESCRIPTION OF THE INVENTION

Figure 1A:
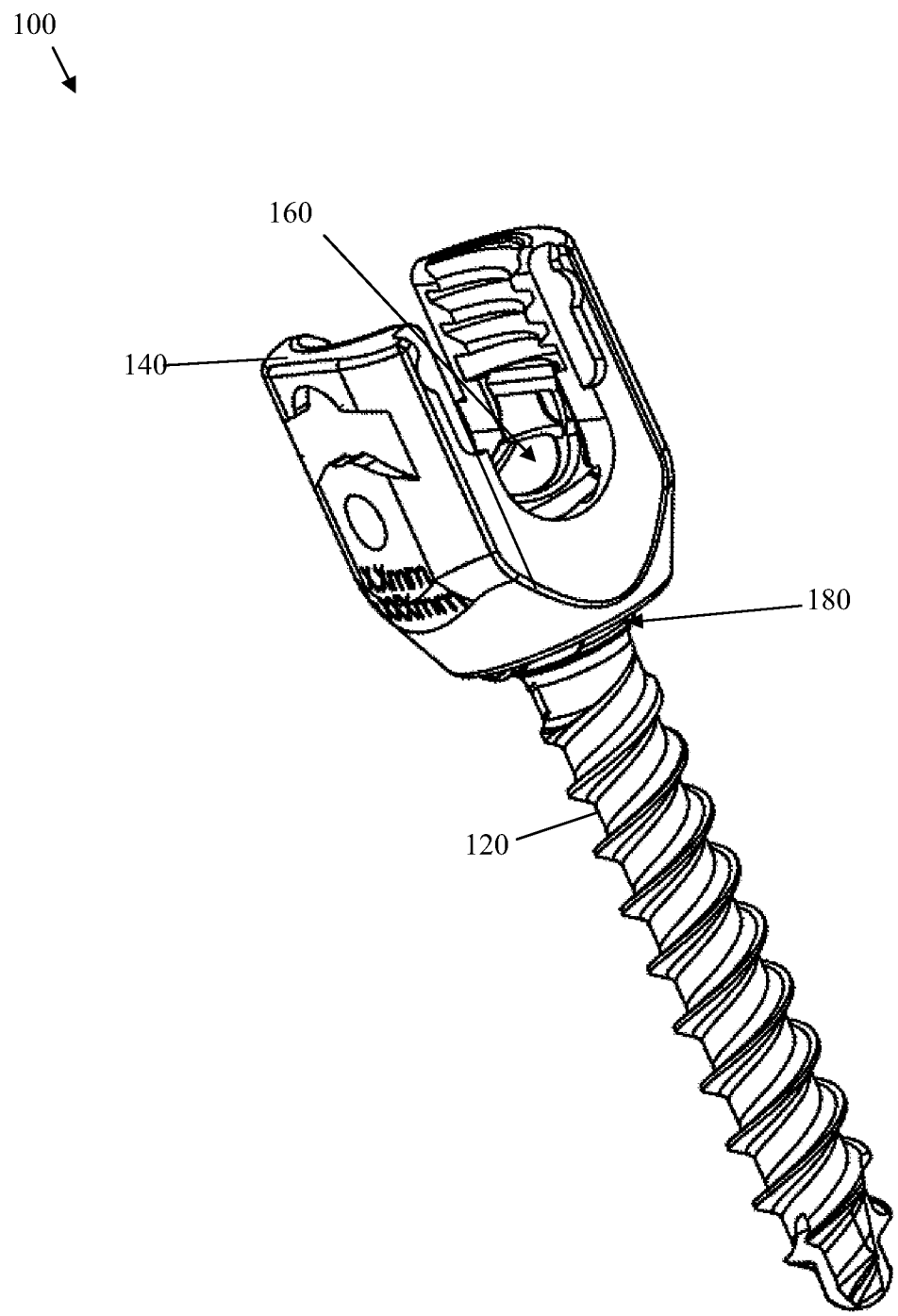
FIG. 1A is a perspective view of the Screw assembly.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Reference to the features of the present disclosure may also be described with respect to coronal, sagittal, and transverse axes of the body. The coronal axis refers to an axis running substantially from front (anterior) to back (posterior) of the body and extending through the mid-section. The sagittal axis refers to an axis running substantially from left to right of the body and extending through the mid-section to intersect the coronal axis at a right angle. The transverse axis refers to an axis running substantially from head to toe of the body and crossing the point where the coronal and sagittal axes intersect at a right angle. Furthermore, the coronal, sagittal, and transverse planes refer to the standard definitions associated with each term. Namely, the coronal plane being a plane perpendicular to the coronal axis and formed by the transverse and sagittal axes, the sagittal plane being perpendicular to the sagittal axis and formed by the coronal and transverse axes, and the transverse plane being perpendicular to the transverse axis and formed by the sagittal and coronal axes.

Generally speaking, a screw assembly 100 comprises a screw 120 operably coupled with a body member 140, a bushing 160 employed within the body member 140, and at least one insert 180 operably coupled with the screw 120, as shown in FIGS. 1A-1F. Generally, the screw assembly 100 includes a longitudinal axis 102 running from the proximal end to the distal end of the screw assembly 100, a transverse axis 104 running perpendicular to the longitudinal axis 102 of the Screw assembly 100, and a lateral axis 106 running perpendicular to the transverse axis 104 and longitudinal axis 102. Upon insertion into a patient, the longitudinal axis 102 may be substantially parallel to a coronal axis of the body, the transverse axis 104 may be substantially parallel to a sagittal axis of the body, and the lateral axis may be substantially parallel to a cranial-caudal axis of the body.

The screw assembly 100 may be used with at least one other such assembly and a stabilization or fixation rod 190 to connect the assemblies and stabilize the vertebras into which the assemblies are inserted. Generally, the body member 140 may rotate 360 degrees relative to the screw 120 about the longitudinal axis 102. In other embodiments, the body member 140 may be restricted from rotation about the longitudinal axis 102. The body member 140 rotates or pivots relative to the screw 120 in only one other direction by operation of the insert 180 rotatably coupled with the body member 140 and the screw 120. In one embodiment, the body member 140 is restricted to rotation about a single other axis, the transverse axis 104, or along the cephalad-caudal plane, and the body member 140 is prevented from rotating or pivoting about the lateral axis 106 or along the medial-lateral plane. The orientation of the features could be adjusted to limit the motion or rotation in any plane desired (medial/lateral, or cephalad/caudal).

Figure 1B:
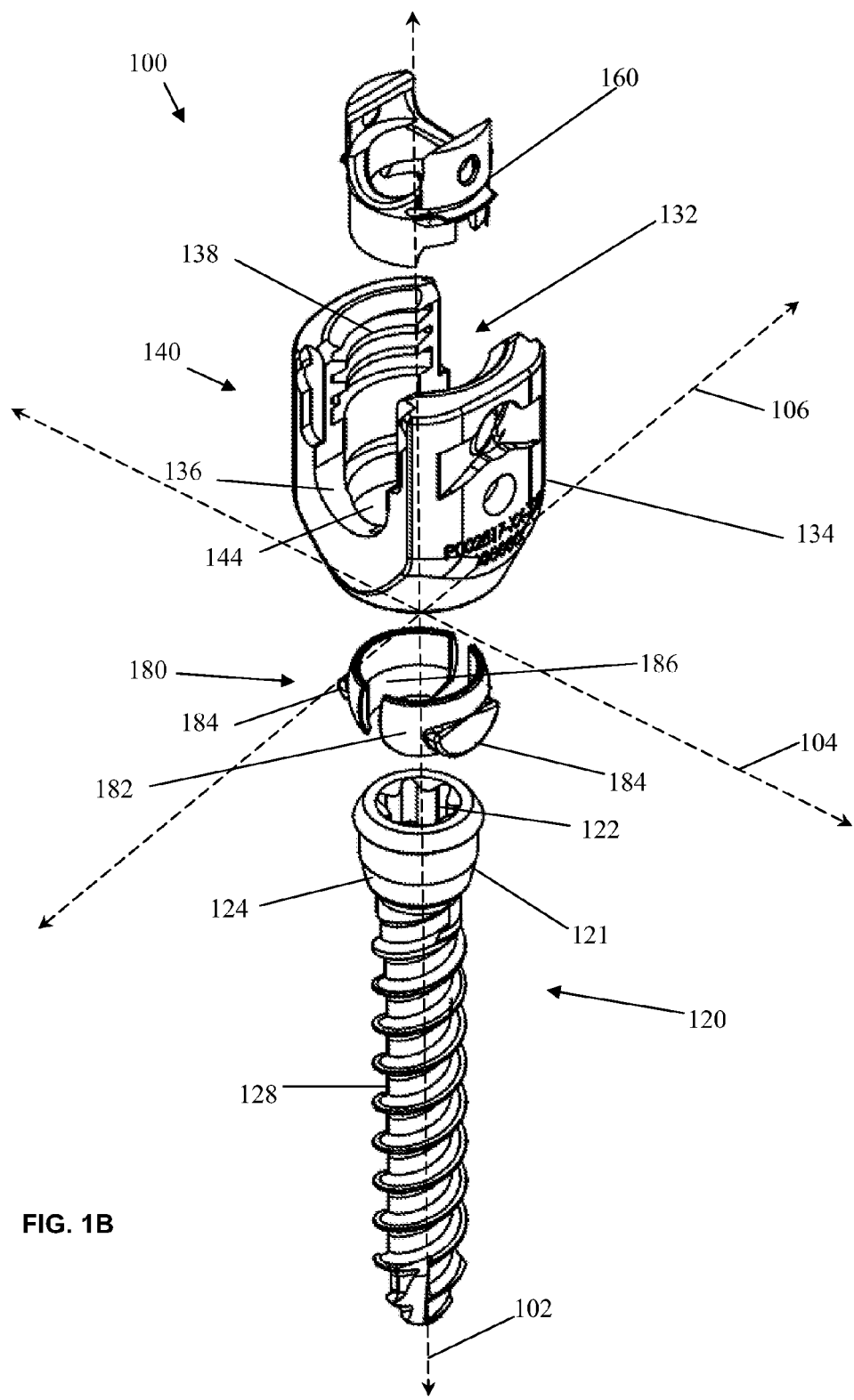
FIG. 1B is an exploded view of the Screw assembly from FIG. 1A.
Figure 1C:
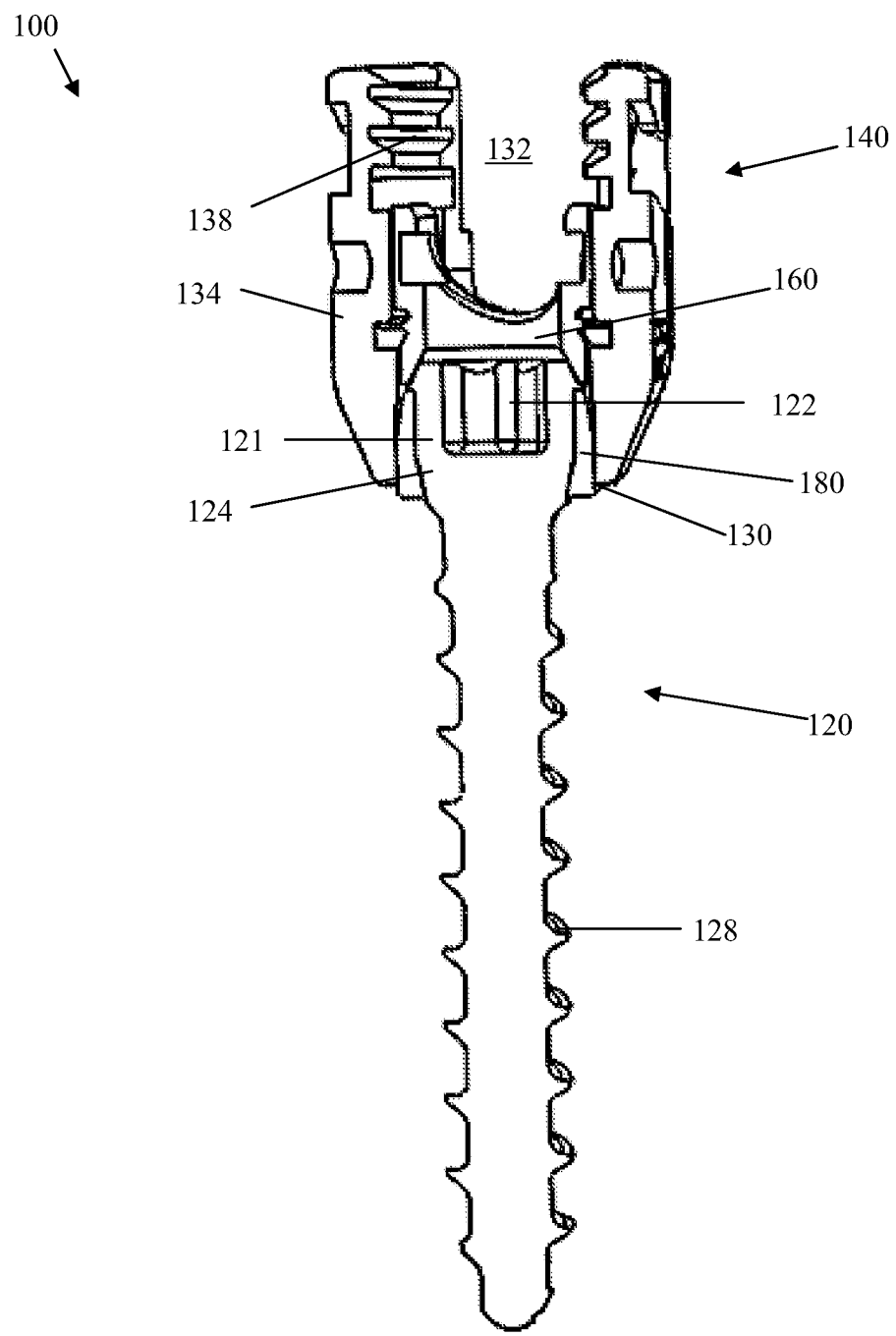
FIG. 1C is a cross-sectional view of the Screw assembly from FIG. 1A.

As shown in FIGS. 1A-1F, the screw 120 includes a head portion 121 on the proximal portion, which defines a slot 122 therein used to drive the screw 120 into the bone. A threaded shaft portion 128 of screw 120 extends therefrom through the body member 140, as shown in FIG. 1C. The head portion 121 includes a lipped surface 124 defined by the lower portion of head portion 121 that rests upon and mates with a rounded interior surface 186 formed in the inner or lower end of the insert 180. The lipped surface 124 allows the head portion 121 to sit within the insert 180 while permitting the head portion 121 of the screw to rotate about its longitudinal axis. The lipped surface 124 may include or form a recessed portion, channel, or groove in a lateral surface of the head portion 121. The channel may be disposed circumferentially about the head portion 121. In one embodiment, the head portion 121 includes a height H1. The head portion 121 includes a cap 126 extending beyond the top portion of the head portion 121 that engages a top portion 188 of the insert 180.

The top portion 188 of the insert 180 allows the cap 126 and the screw 120 to rotate about its longitudinal axis without moving distally. The exterior surface of the cap 126 includes a curved surface that substantially aligns with exterior surface 182 of the inserts 180 so to form a continuous curved exterior surface thereabout, as shown in FIG. 1F, which permits the body member 140 to rotate about exterior surface of the cap 126 and exterior surface 182 of the insert 180. The insert 180 includes at least two extensions 184 projecting from an exterior surface 182 of the insert 180 to operably engage the interior surface of the body member 140, so as to allow the body member 140 to rotate relative to the screw 120 only in one plane or along the traverse axis 104, while limiting rotation in a plane perpendicular to the transverse axis 104.

The extensions 184 may be symmetrical and facing opposite directions or be in substantial parallel alignment about the circumference of the insert 180 or head portion 121 of the screw 120, which restricts the rotation of the body member only about the transverse axis 104 or in a single plane. The insert 180 may be a single construction or divided up into a plurality of portions or segments; however, the extensions 184 may be symmetrical about the circumference of the insert 180. In one embodiment, the head portion 121 includes a Width W1 around the circumference of the head portion 121. The inserts 180 allow for operably coupling with any sized head portion 121 of the screw, any screw shank design, and any thread pitch. The head portion 121 includes a diameter D1, as shown in FIG. 1E, wherein the insert 180 may be sized to fit around diameter D1 of any size. The inserts 180 also can be loaded from the bottom to allow for larger diameter shanks to be used.

Figure 2A:
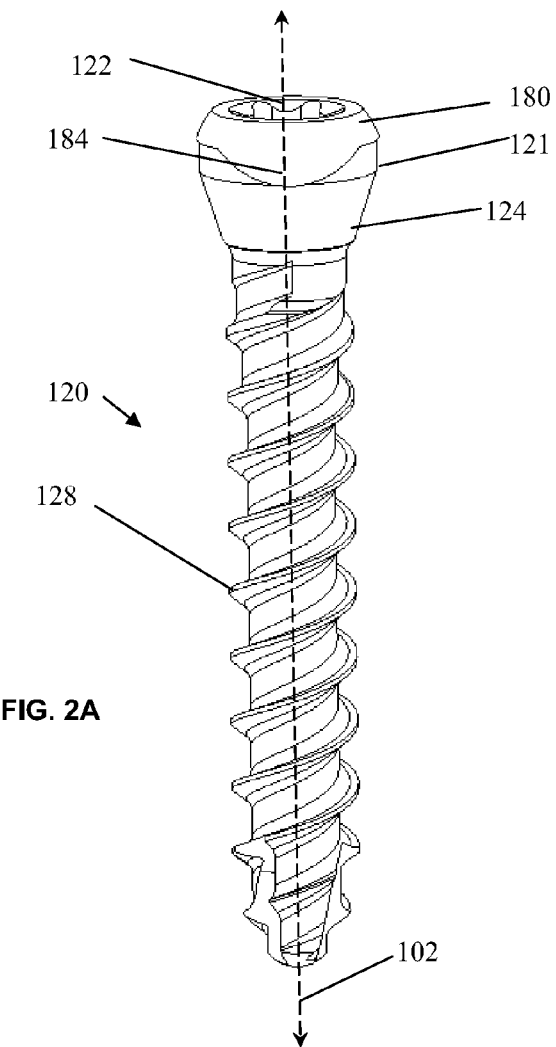
FIG. 2A is a side view of an alternative embodiment of the screw.
Figure 2B:
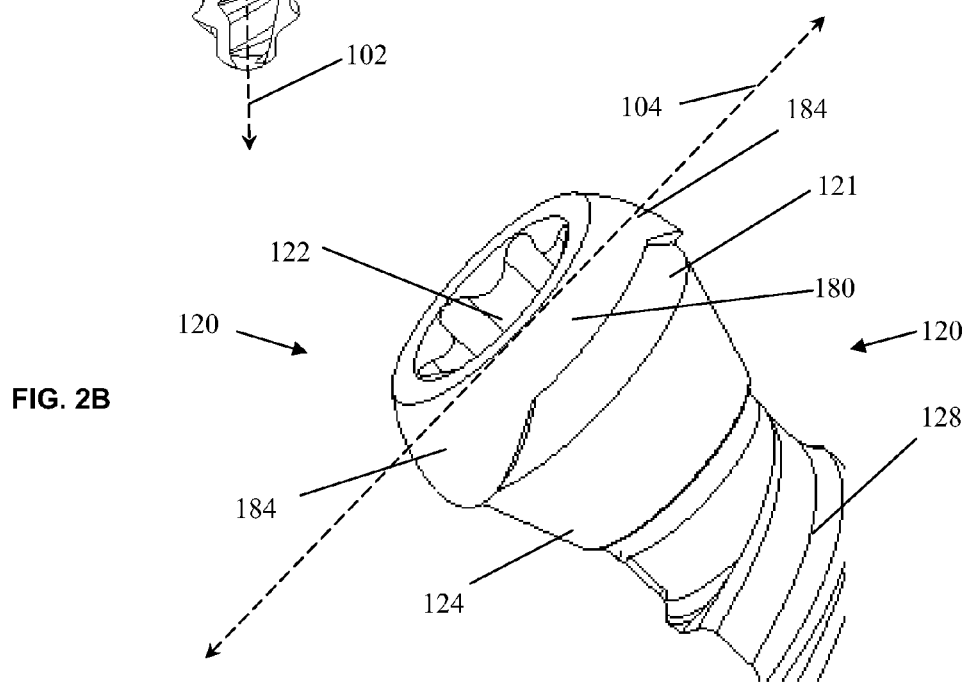
FIG. 2B is a perspective view of the alternative embodiment of the screw head portion.

In alternative embodiment, the insert 180 is integral with the head portion 121 of the screw 120, as shown in FIGS. 2A-2B. The extensions 184 are on opposite sides of the insert 180 that is integral with the head portion 121, such that the when the extensions 184 are operably coupled with the body member 141, the screw 120 is unable to rotate about its longitudinal axis 102 relative to the body member 140, but is able to rotate or pivot about the transverse axis 104. In this embodiment, the head portion 121 does not include the cap 126 and the head portion 121 is unable to rotate about the longitudinal axis 102 when insert 180 and the extension 184 are mounted within the body member 140.

Figure 3A:
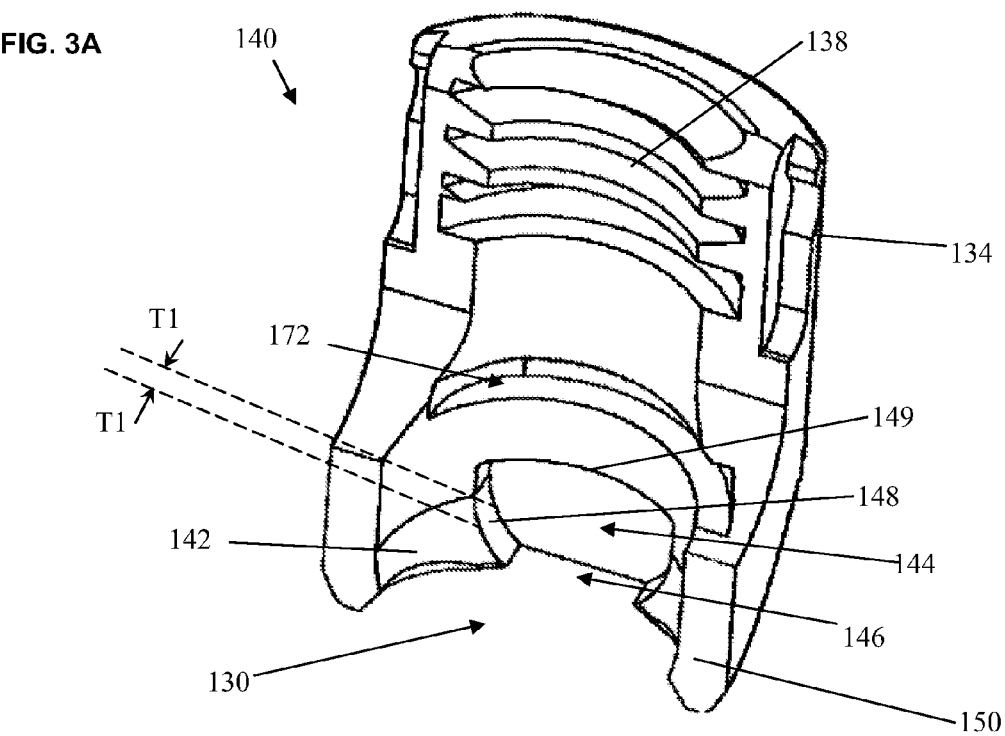
FIG. 3A is a cross-sectional perspective view of the body member, according to one embodiment.
Figure 3B:
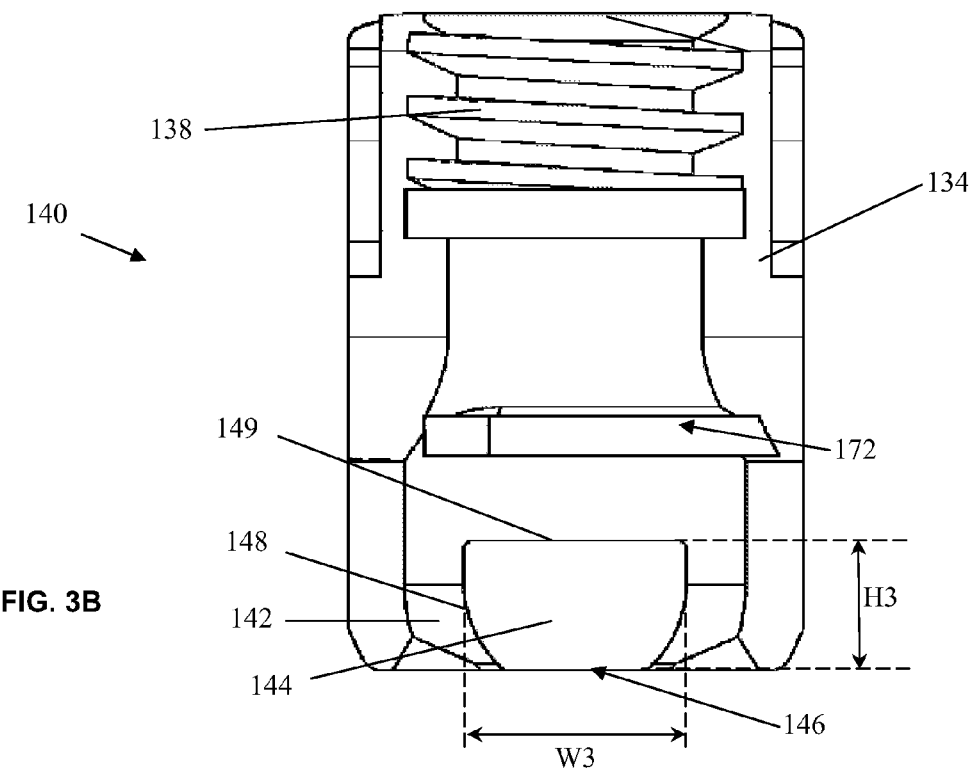
FIG. 3B is a cross-sectional side view of the body member, according to one embodiment.
Figure 3C:
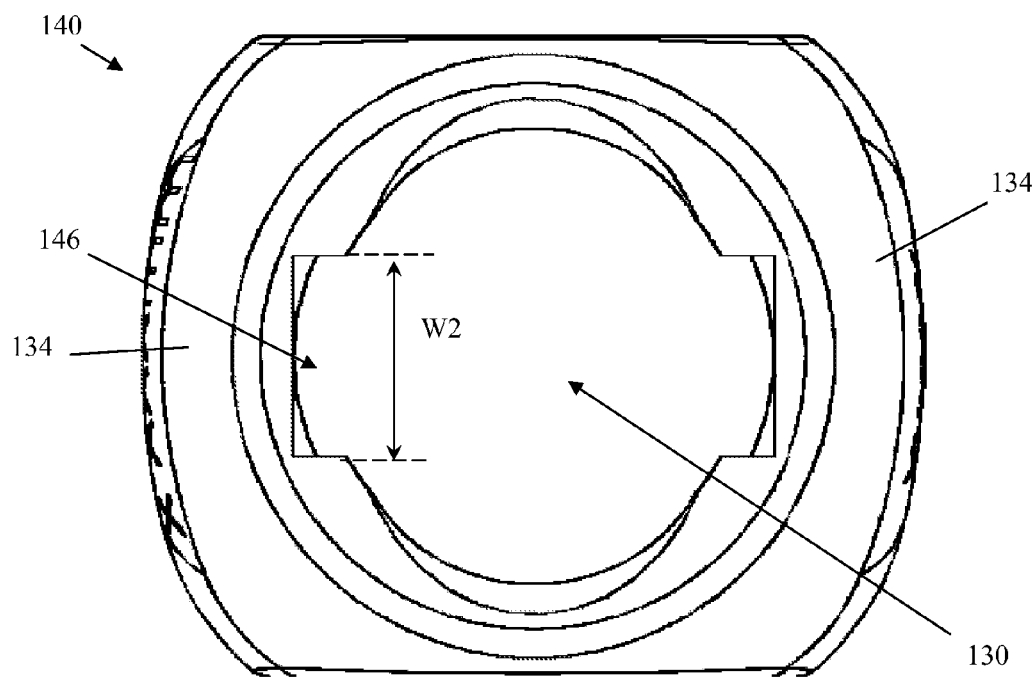
FIG. 3C is a bottom view of the body member, according to one embodiment.
Figure 3D:
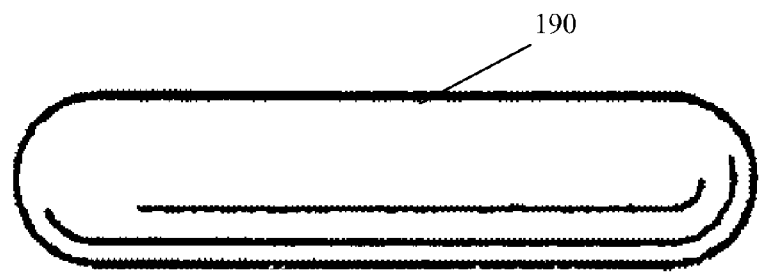
FIG. 3D is a side view of a fixation rod, according to one embodiment.
Figure 6A:
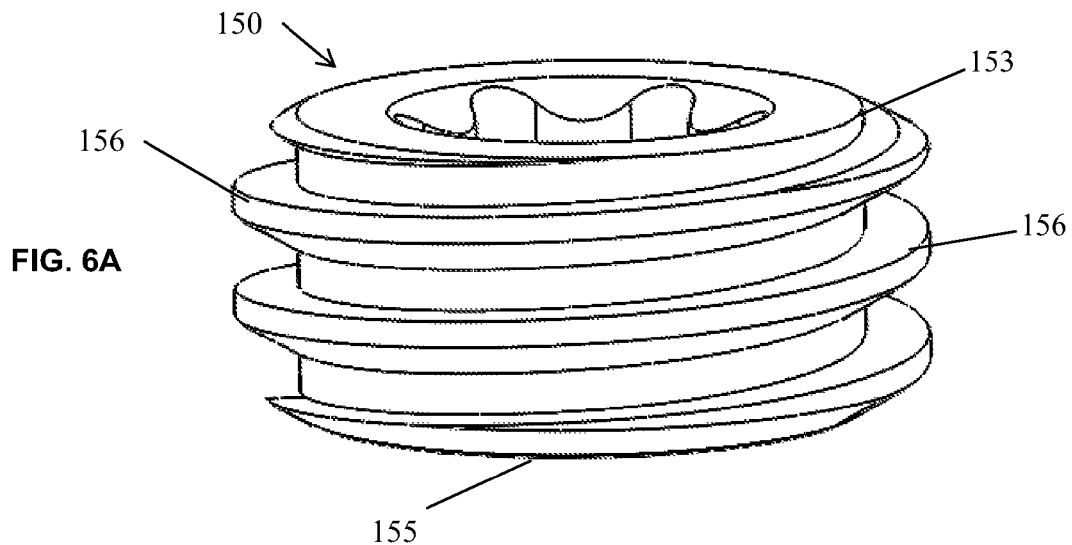
FIG. 6A is a perspective view of the cap, according to one embodiment.
Figure 6B:
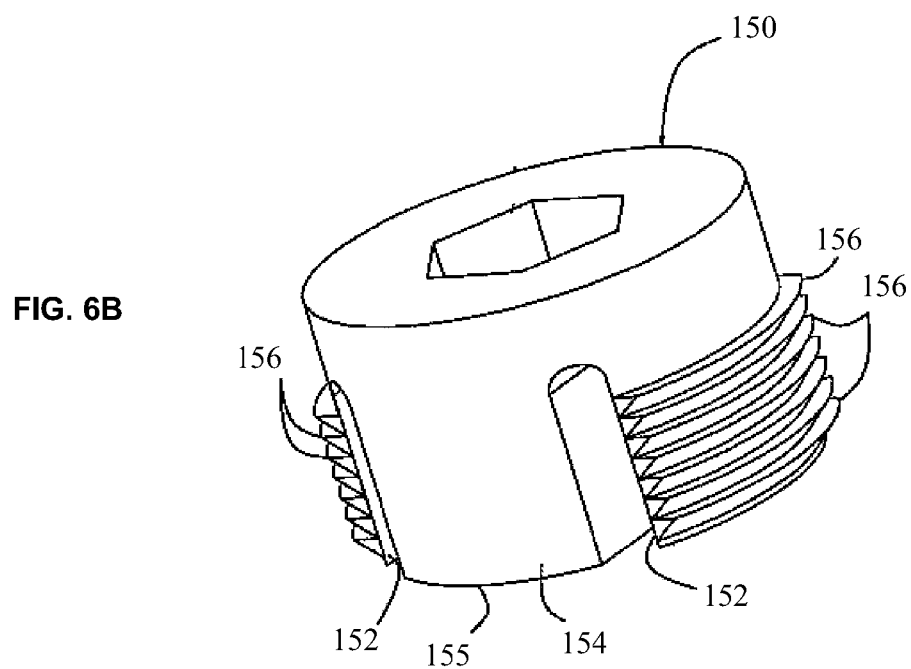
FIG. 6B is a perspective view of the cap, according to one embodiment.

As shown in FIGS. 1B-1C, the body member 140 includes a side wall 134 that defines at least two slots 132 axially disposed through the side wall 134 thereof, where each slot 132 includes a curvilinear surface 136 on the distal ends of the slots 132. The two slots 132 generally form a U-shape and are sized to receive a fixation rod 190 (as shown in FIG. 3D) within the side walls 134. The side walls defining the slots preferably extend upwardly beyond the midpoint of the rod 190 and can be inclined slightly to provide a slight holding force on the rod prior to securing the rod 190 with a locking cap 150 (as shown in FIGS. 6A-6B). Thus, during assembly, the surgeon exerts a slight downward force on the rod 190, snapping the rod 190 into the transverse channel defined by the aligned slots 132.

As shown in FIGS. 1B-1C and 3A-3B, the upper interior surface of side walls 134 of the body member 140 both have radially projecting serrations formed therein defining a plurality threaded portions 138 or axially aligned ratchet teeth 138. The interior distal surface of body member 140 has conical section 142 formed therein and a pair of concave pockets 144. The conical section 142 couples with the exterior surface 182 of the inserts 180 to allow rotation of the body member 140 relative to the insert 180, while the concave pockets 144 mates with the extensions 184 on the inserts 180, as to provide a rotational motion of the body member 140 with respect to the screw 120. The concave pockets 144 include a lower opening 146 connected to two curved side walls 148, while the two curved side walls 148 connect to a top portion 149. Preferably, the top portion 149 is substantially straight from the connecting points of the two curved side walls 148. In one embodiment, the concave pocket 144 includes a height H3 from the top portion 149 to the lower opening 146. In one embodiment, the lower opening 146 includes a width W2. In one embodiment, the curved side walls 148 and the top portion 149 include a thickness T1.

To secure the fixation rod 190 within the body member 140 of the assembly, a locking cap 150 is provided as shown in FIGS. 6A and 6B. One exemplary cap, as described in U.S. Pat. No. 7,377,923, incorporated by reference in its entirety, defines a top portion, a pair of opposed arcuate depending leg portions and a centrally disposed depending projection equidistantly spaced from leg portions. Central projection preferably defines a planar lower or bottom surface. The leg portions of cap each have a plurality of radially projecting serrations formed therein that define a plurality of axially aligned ratchet teeth adopted to engage teeth 138 on the opposed interior side walls 134 of the body member 140, as will be described in U.S. Pat. No. 7,377,923. Alternatively, the cap includes a threaded portion to operably engage the threaded portion 138 of the interior side walls 134 of the body member 140. For example, in FIG. 6A, the cap 150 may include a setscrew as known in the art.

As shown in FIGS. 4A-4D, each insert 180 includes at least one extension 184 extending from the curved exterior surface 182. The extension 184 includes a top portion 192 and a substantially curved bottom portion 194. The curved bottom portion 194 includes a radius of curvature R1 that substantially aligns with the two curved side walls 148 of the concave pocket 144 in the body member 140. The curved bottom portion 194 includes a radius of curvature R1 that fits within the lower opening 146 with width W2, such that the curved bottom portion 194 may rotate within the lower opening 146 of the concave pocket 144. The top portion 192 includes two angled surfaces 192a and 192b with an angle of decline A2. The angle of decline A2 determines the amount of rotation for the body member 140 relative to the screw 120, as rotation will abut one of the angled surfaces 192a, 192b with the top portion 149 of the concave pocket 144 and cease rotation of the body member 140 relative to the screw 120. The insert 180 also includes a top portion 188 of the exterior surface 182, and the top portion 188 of the exterior surface is separated by a distance D2 from the top portion 192 of the extension 184.

Figure 4A:
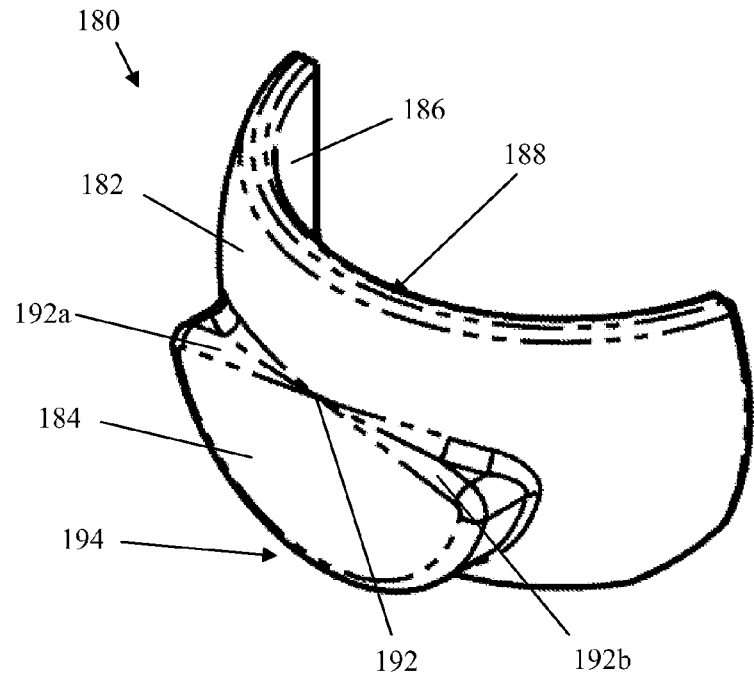
FIG. 4A is perspective view of the insert, according to one embodiment.
Figure 4B:
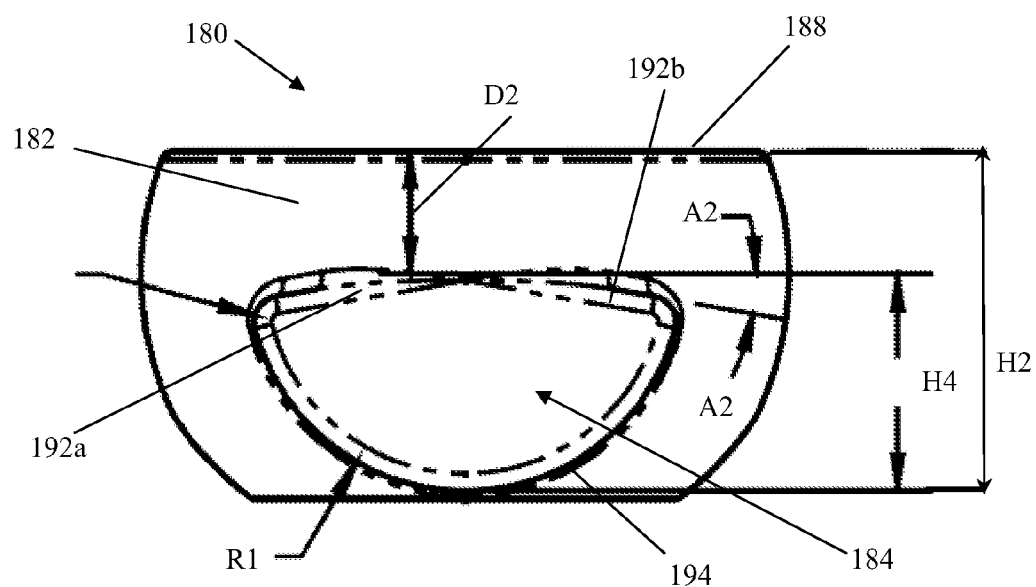
FIG. 4B is a side view of the insert, according to one embodiment.

In one embodiment, the insert 180 includes a height H2 from the top portion 188 to the bottom of the exterior portion 182, as shown in FIG. 4B. In one embodiment, the height H2 of the extension 184 is substantially equal to the height H1 of the head portion 121 of the screw 120. In one embodiment, the extension 184 includes a height H4 from the top portion 192 to the bottom of the bottom portion 194. In one embodiment, the height H4 of the extension 184 allows the extension 184 to fit within the concave pocket 144 and the height H3 of the concave pocket 144, as to allow the extension 184 to rotate within the concave pocket 144. The height H4 of the extension 184 may be smaller than the height H3 of the concave pocket. Alternatively, the height H3 of the concave pocket 144 relative to the height H4 of the extension 184 may be adjusted to allow for increased or decreased rotation of the body member 140 relative to the insert 180, whereby an increased height H3 of the concave pocket 144 relative to the height H4 of the extension 184 provides for an increased rotation, and an decreased height H3 of the concave pocket 144 relative to the height H4 of the extension 184 provides for a decreased rotation. The increased height H3 of the concave pocket 144 relative to the height H4 of the extension 184 allows for the top portions 192a, 192b to rotate higher/proximally and engage the top portion 149 of the concave pocket 144 at an increased angle.

In one embodiment, the range of rotation is about +/−40° about the transverse axis 104 (as measured from the longitudinal axis 102 of the screw) alternatively about +/−30° about the transverse axis, alternatively about +/−20° about the transverse axis, for a total motion rotational range of between about 20° and 80° about the transverse axis without permitting any rotation about the caudal-cranial axis. This exemplary extended range of motion, while limiting the rotation motional along the axis perpendicular to the transverse axis, allows the surgeon additional freedom in locating the screws and eases the assembly process by reducing the requirement for a rod contouring. In some examples, rotation may be permitted about the caudal-cranial axis and while rotation about the transverse axis may be prohibited.

As shown in FIG. 4C, in one embodiment, the extension 184 includes a thickness T2 that fits within the thickness T1 of the curved side walls 148 and top portion 149 of the concave pocket 144. In one embodiment, the insert 180 includes a width W4 such that the insert fits around at least a portion of the head portion 121 of the screw 120 and around at least a portion of Width W1 of the head portion 121. As shown in FIG. 4D, in one embodiment, the extension 184 includes a Width W5 such that the extension 184 fits within the concave pocket 144 and Width W3, while the concave pocket 144 is able to rotate about the extension 184.

Figure 4E:
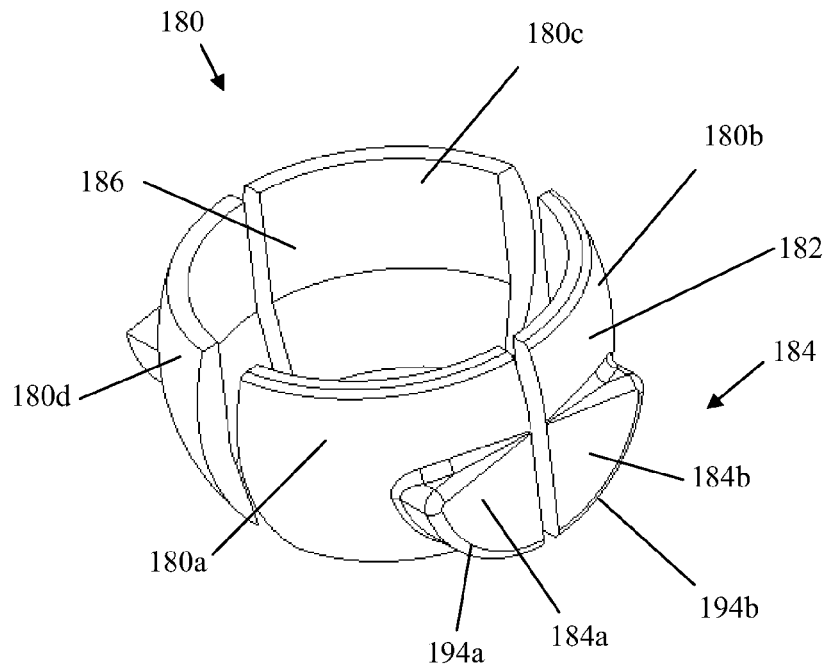
FIG. 4E is perspective view of an alternative embodiment of the insert including a plurality of portions.

Alternative embodiments of the insert 180 are shown in FIGS. 4E-4H. In one embodiment, as shown in FIG. 4E, the insert 180 may include a plurality of insert portions 180a, 180b, 180c, 180d, whereby the extension 184 also includes at least a first extension portion 184a and a second extension portion 184b. The first insert portion 180a includes the first extension portion 184a and the second insert portion 180b includes the second extension portion 184b. Preferably, the first extension portion 184a and the second extension portion 184b each represent half of the extension member 184. The first extension portion 184a may be symmetrical with the second extension portion 184b, or the first extension portion 184a may be asymmetrical with the second extension portion 184b. The asymmetry with the first extension portion 184a and the second extension portion 184b allows for the first curved bottom portion 194a to be different than the second curved bottom portion 194b and include a different radius of curvature R1 if different angles of rotation are desired along the transverse axis. The plurality of insert portions 180a, 180b, 180c, 180d couple with the head portion 121 to form the rounded interior surface 186 and the curved exterior surface 182.

Figure 4F:
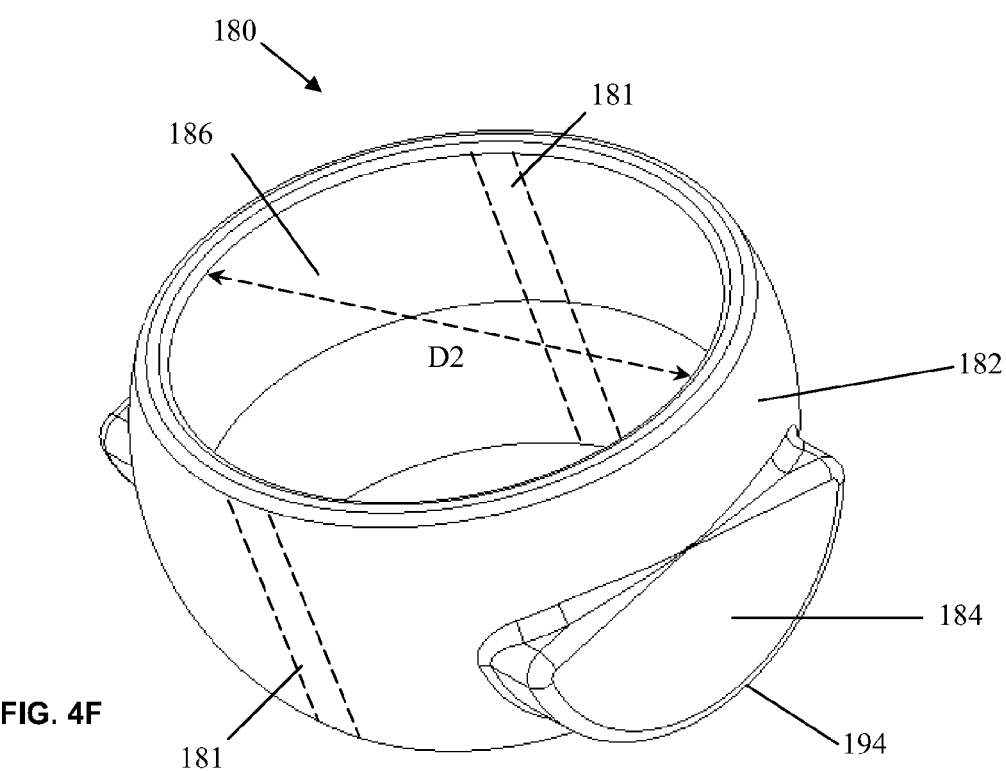
FIG. 4F is a perspective view of an alternative embodiment of the insert in a unitary piece construction.
Figure 4G:
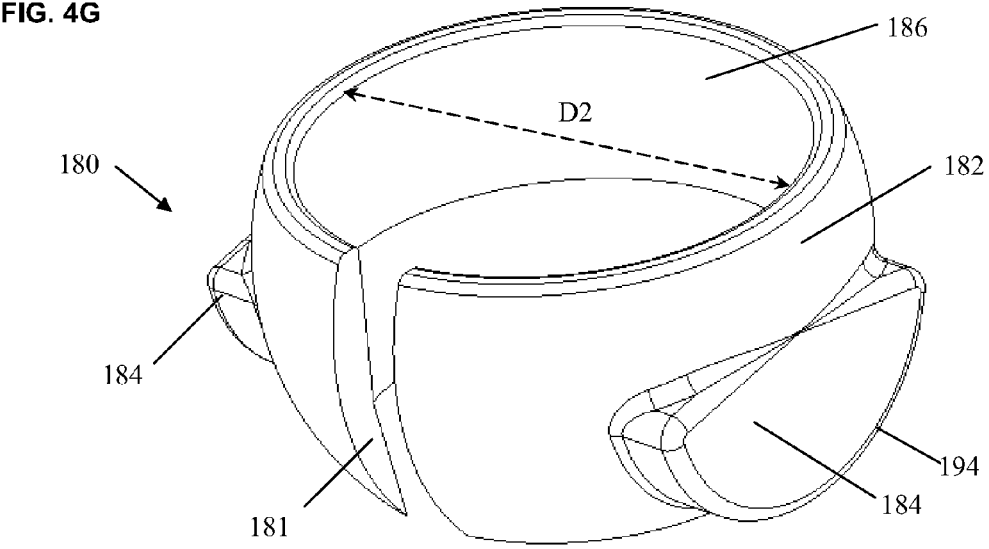
FIG. 4G is a perspective view of an alternative embodiment of the insert in a unitary piece construction with a vertical opening for expansion.

An alternative embodiment of the insert 180 is shown in FIG. 4F, whereby the insert 180 is substantially a single piece including the rounded interior surface 186 to fit about the head portion 121 of the screw, as to allow rotation of the head portion 121 within the rounded interior surface 186 of the insert 180. The insert 180 may include a cut 181 extending through the exterior surface 182 to the interior surface 186 to enable circumferential expansion of the insert 180 to ease assembly with the screw 120, body member 140, and bushing 160. The insert includes a diameter D2, which may be expanded by allowing separate portions or segments of the insert 180 to expand around the diameter D1 of the head portion 121. The cut 181 may be removed from the exterior surface 182 and interior surface 186, as shown in FIG. 4G, as to form a C-shape insert 180 that circumferentially expands diameter D2 to be operably coupled with head portion 121 of the screw 120.

Figure 4H:
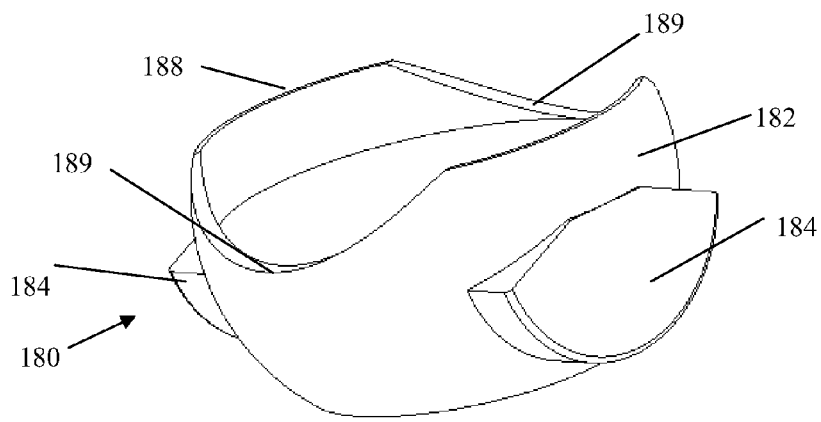
FIGS. 4H-4I are perspective views of an alternative embodiment of the insert including curved top portions.
Figure 4I:
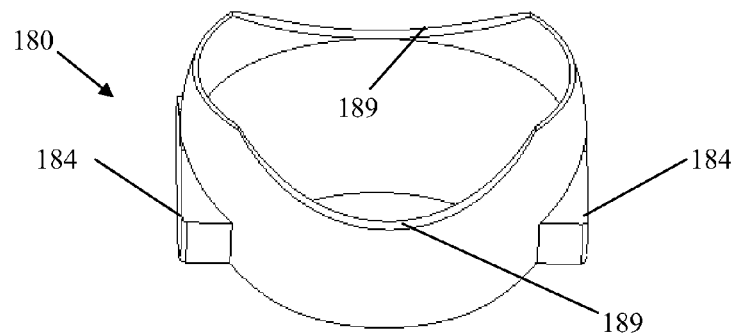

An alternative embodiment of the insert 180 is shown in FIGS. 4H-4I, whereby the top portion 188 includes at least two curved portions 189 that are perpendicular to the extensions 184. The curved portions 189 are on opposite sides of the insert 180 and prevent the insert 180 from rotating or pivoting about an axis perpendicular to the transverse axis. Alternatively, the curved portions 189 may engage with the bushing 160, as to prevent the head portion 121 from rotating about its longitudinal axis.

Figure 5A:
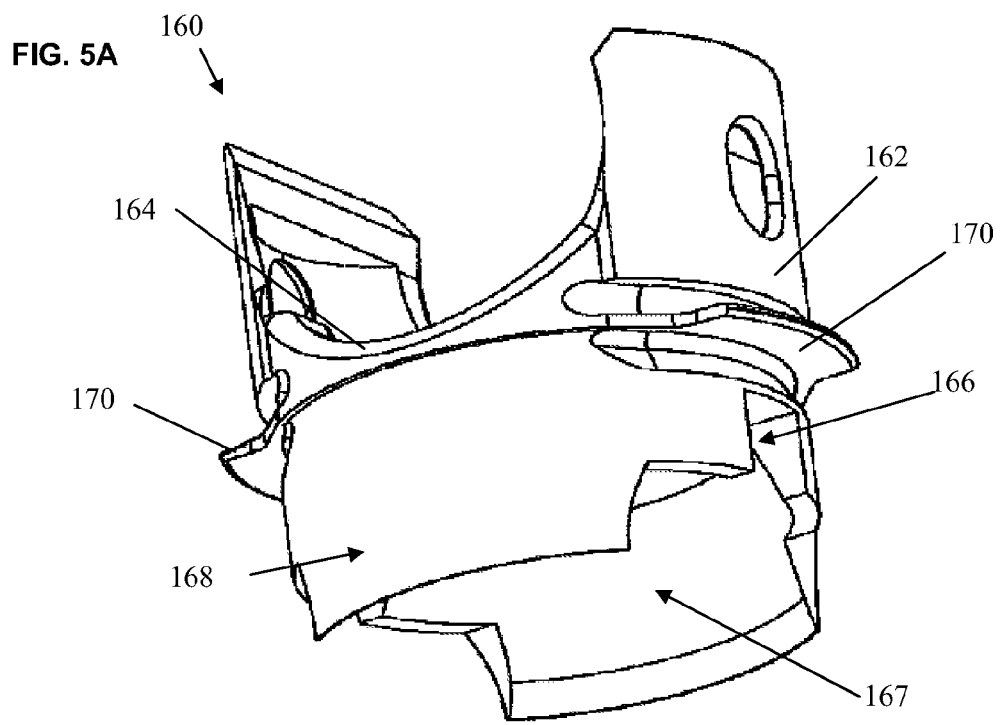
FIG. 5A is a perspective view of the bushing, according to one embodiment.
Figure 5B:
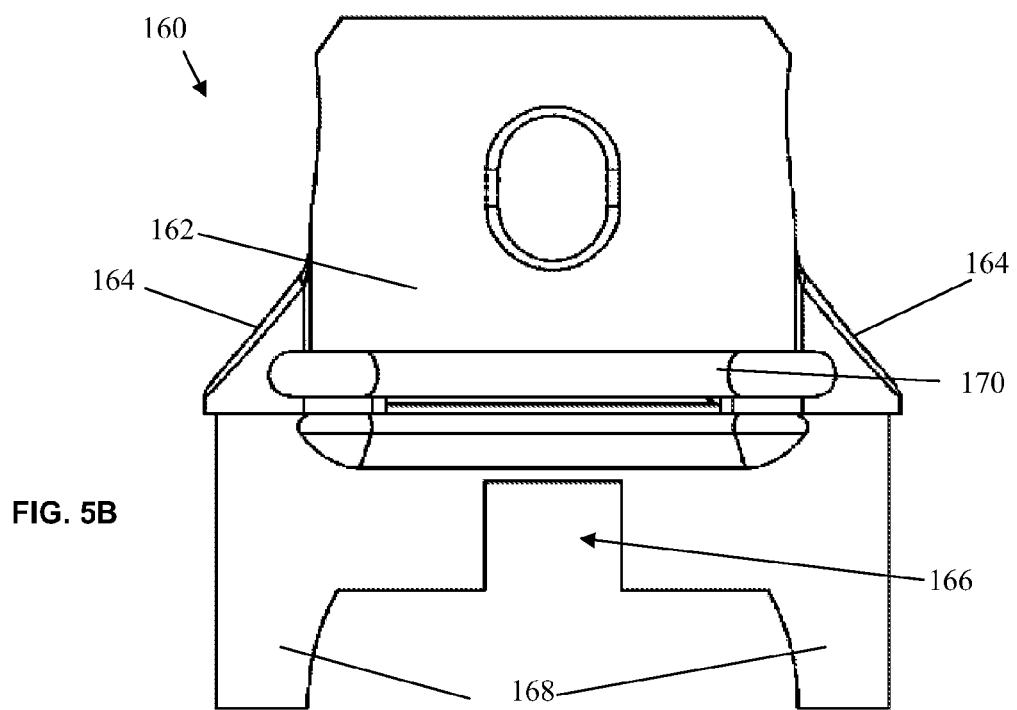
FIG. 5B is a side view of the bushing, according to one embodiment.

As shown in FIGS. 5A-5B, the bushing 160 is preferably employed within the body member 140 of the assembly 100 adjacent to side walls 134 to better distribute the longitudinal forces exerted on the pedicle screw 120 by the cap 150 and rod 190. The bushing 160 defines a pair of opposed concave surfaces 164 formed in the upper end of a circular skirt 162 so as to define a seat for the fixation rod 190. The skirt may generally form a U-shape channel that coincides with the curvilinear surface 136 of the body member 140 and seat therein for the rod 190. The lower portion of bushing 160 includes slots 166 to provide flexibility therein and defines depending tapered ends 168 to form a conical lumen 167 adapted to abut opposed sides of the head portion 121 and cap 126 and allow rotation of the body member 140 about the head portion 121 and insert 180.

A pair of outwardly projecting opposed resilient tabs 170 are provided at the upper ends of the bushing 160 between the top ends of the bushing skirt 162 that in some embodiments are adapted to be received in a snap fitment within a pair of opposed apertures 172 (shown in FIGS. 3A-3B) formed on the inside of the side wall 134 of body member 140 whereupon the rod seat in bushing 160 is aligned with the channel 132 in the body member 140. Note that in the illustrated embodiment shown in FIGS. 3A and 5A, for example, the resilient tabs 170 will engage with the body member 140 inner cylindrical surface located below the ratchet teeth 138, the illustrated aperture 172 being located in the vicinity of the ratchet teeth 138 that cooperate with the locking cap 180 and thus at a distance from the bushing 160. In an alternative embodiment, the tabs could be removed from the bushing 160 and located on the body member 140 for engagement with apertures or other receiving structure or members formed in opposed sides of the bushing.

To provide a basic stability to the system during initial assembly, the bushing 160 with its slotted lower skirt portion can be configured to provide a press fitment about the screw head 120 so that the pedicle screw 120, body member 140 and bushing 160 will not move freely prior to the insertion and securement of the fixation rod 190. In other examples, movement may be limited due to partial press fitment. For example, the bushing 160 may provide a variable press fitment to provisionally lock the body member 140 and pedicle screw 120. In addition, the upper portion of the bushing could be configured such that the wall surfaces 164 defining the rod seat therein extend upwardly past the midpoint of the rod and are slightly inwardly inclined. This would provide the same slight holding force when the rod 190 is pushed into the bushing seat 164 that was above described with reference to the channel walls 135 in the body member 140 of the assembly 100.

Upon securing the bushing 160 in the body member 140 and the fixation rod 190 in bushing seat 164, the locking cap 150, as shown in FIGS. 6A-6B, may be used to rigidly fix the assembly to the rod 190 to the screw assembly 100. The locking cap 150 includes a screw or threaded portion 156 about its exterior surface from the top portion 153 of the locking cap 150 to the bottom portion 155 of the locking cap 150, as shown in FIG. 6A. The locking cap 150 aligns within the side walls 134 of the body member 140 and the threaded portion 156 engages the threaded portion 138 of the interior side walls 134, such that the locking cap 150 may move distally within the body member 140 and lock down on the bushing and apply a distal force on the bushing.

Alternatively, as shown in FIG. 6B, the cap 150 includes depending leg portions 152 thereon to aligned with the side walls 134 of body member 140. Upon pressing the cap 150 downwardly into body member 140, the ratchet teeth 138 and 156 on the body member 140 and cap 150 interlock so as to allow the cap to be pressed downwardly but not proximally retracted. As cap 150 is pressed downwardly into the body member 150 of the assembly, the planar bottom surface 155 of the central projection 154 thereon abuts the fixation rod and presses the rod into and against the seat 164 formed on the upper end of bushing 160. The resulting pressure on the bushing causes the tapered surfaces 168 on the lower end of the bushing to press against the rounded surface of the screw head 120, thereby securing the rod in seat 164 and providing decentralized and evenly distributed force acting along the longitudinal axis of the screw.

In use, at least two of the pedicle screws 120 with the body members 140 and attached bushings 160 disposed about the screw are inserted into the pedicles of adjacent vertebrae, spanning the vertebral region to be fixated. The surgeon preliminary contours the fixation rod and checks the alignment between the rod and the mating channels formed by the slots in the bushing and body member of the assemblies. Since additional contouring is usually required to improve the alignment, the surgeon incrementally adjusts the rod shape and checks the fit within the channels until the rod properly fits in all channels.

Figure 7A:
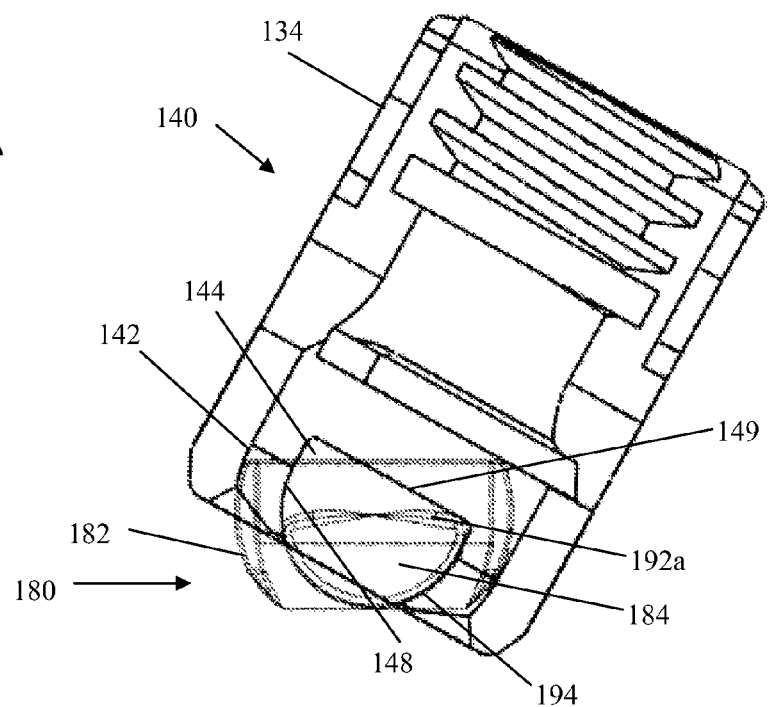
FIG. 7A is cross-sectional view of the body member and the insert shown in phantom, when the body member is rotated about the transverse axis.
Figure 7B:
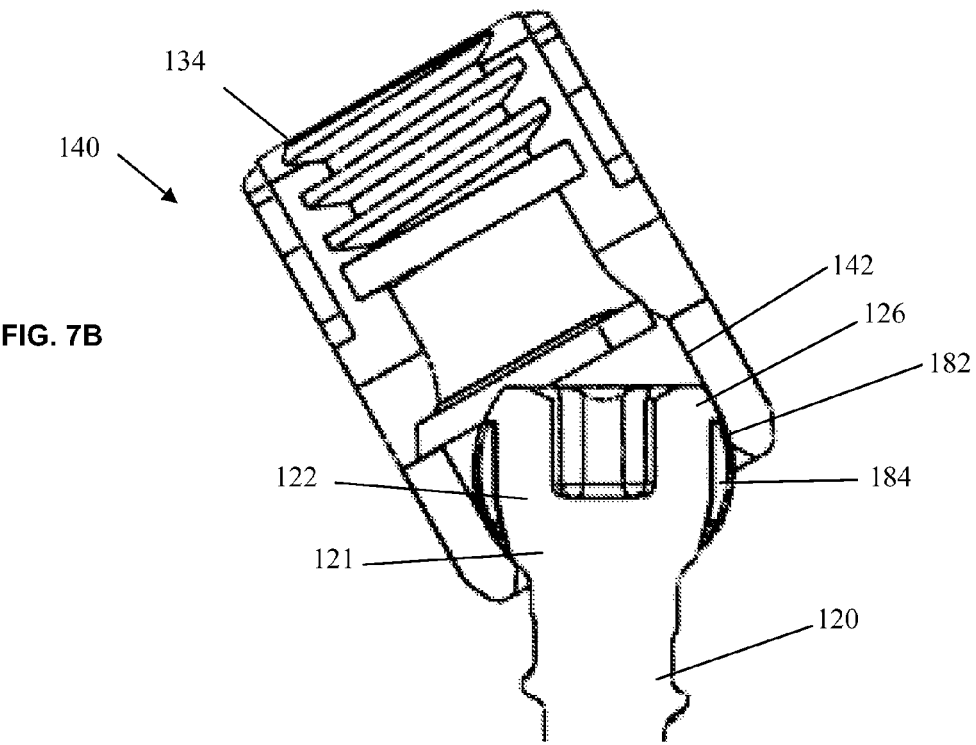
FIG. 7B is a cross-sectional view of the body member and the screw, when the body member is rotated about the transverse axis.

During the contouring process, the body member 140 may be rotated in only one plane relative to the insert, as shown in FIGS. 7A-7B. The body member 140 is rotated in only one plane when rotated by an operator to allow the concave pocket 144 to rotate about the extension 184 of the insert 180, where the curved bottom portion 194 of the extension 184 slides along the two curved side walls 148 of the concave pocket 144 in the body member 140, as shown in FIG. 7A. The exterior surface 182 of the insert 184 slides against the conical section 142 of the body member 140 while the body member 140 rotates about the insert 184, as shown in FIG. 7B. The top portion 192a of the extension 184 engages or abuts the top portion 149 of the concave pocket 144, which stops rotation of the body member 140 relative to the insert 180.

The bushing 160 may be inserted during initial assembly of the screw 120 and the body member 140. The bushing applies force to the top of the head portion 121 that sits above the insert 180 as well as contacts and applies force to the inserts themselves. The force from the bushing 160 is then transferred through the insert 180 to the screw 120 to lock motion in all directions. When the locking cap 150 is inserted, it applies force to the bushing 160 which then applies force to the screw 120 and the insert 180. Then, the locking cap 150 can be mated with the body member 140 (by pressing the cap axially into the body member to create the interlock between the ratchet teeth on the body member and the cap) to temporarily hold the rod in place, thereby assisting the surgeon in achieving an accurate fit. The locking caps are then easily removable (by rotating the cap a quarter of a turn to disengage the interlocking teeth or disengage the threads), allowing the rod to be further contoured.

Once properly contoured, the rod is inserted into the channels and a locking cap is pressed tightly into each body member and bushing to secure the rod in place. To effect securement of the rod at each of the pedicle screw assemblies, it is solely necessary to drive the locking cap longitudinally into the body member such that the bottom surface 155 of the central projection 154 on the cap presses against the fixation rod, causing the rod to press downwardly against the bushing 160, which in turn mates with and presses against the head of the pedicle screw.

In another embodiment, the bushing 160 is not employed. The opposed axial slots 132 in the side wall 134 of the body member 140 of the assembly define a seat for the fixation rod 190. When the locking cap 150 is pressed into the body member 140 with the fixation rod extending there-across, the planar bottom surface 154 of the central projection 152 again abuts the fixation rod and, in this instance, presses the rod against the upper end of the head of the pedicle screw. For such applications, the body member and pedicle screw would be sized such that the upper surface of the screw would project above the bottom of the seat defined by the axially opposed slots 132 so as to enable the rod to press against the screw and create a rigid, yet adjustable, securement between the body member and the pedicle screw. In all of these embodiments, the components of the screw assembly are preferably formed of titanium, although any metal, polymer, or composite thereof may be employed.

It should be noted that while the preferred configuration of the locking cap provides a rounded and flush mounting on the upper ends of the body member 140 when the locking cap is fully inserted against the fixation rod, other locking cap configurations could be employed. For example, FIG. 6B illustrates a locking cap having a generally cylindrical perimeter portion in which the ratchet teeth 156 project radially therefrom along leg portions 150. As a result, the upper end of the locking cap would be inwardly offset from the upper end of the body member without adversely affecting the operation of the screw assembly. Various other changes and modifications also could be made in carrying out the present invention.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

What is claimed is:

1. A screw assembly configured to receive a fixation rod, the screw assembly comprising:
    a screw with a longitudinal axis including a proximal end with a head portion and a distal end with a threaded portion;
    an insert operably coupled with the head portion and configured to rotate relative to the head portion about the longitudinal axis, the insert having a pair of extensions projecting radially away from the longitudinal axis; and
    a body member operably coupled with the insert, the insert being rotatably disposed within the body member, the body member having a threaded portion disposed on an interior side wall of the body member, and a pair of opposed recesses disposed beneath the threaded portion, each of the opposed recesses is configured to receive a respective extension of the pair of extensions, the pair of extensions working in concert with the pair of opposed recesses so as to only pivot the body member relative to the insert along an axis orthogonal to both the longitudinal axis and an axis defined by a line transverse to the pair of extensions.

2. The screw assembly of claim 1, wherein the insert further comprises at least a partially curved interior surface configured to engage a curved lateral surface of the head portion.

3. The screw assembly of claim 1, wherein the insert permits 360 degree rotation of the body member relative to the head portion about the longitudinal axis.

4. The screw assembly of claim 1, wherein the extensions are diametrically opposed to each other.

5. The screw assembly of claim 1, wherein the each of the extensions include proximal surfaces that angle away from a plane that is normal to the longitudinal axis by a predetermined angle and are configured to limit pivoting of the body member to a predetermined pivot angle.

6. The screw assembly of claim 1, wherein each of the extensions include distal surfaces that are curved and configured to permit pivoting of the body member.

7. The screw assembly of claim 1, further comprising a bushing disposed between the body member and the head portion.

8. A screw assembly configured to receive a fixation rod, the screw assembly comprising:
    a screw with a longitudinal axis including a proximal end with a head portion having a curved circumferential surface and a distal end with a threaded portion;
    an insert including
        at least a partially curved interior surface that engages the curved circumferential surface to rotate relative to the head portion about the longitudinal axis, the insert having a pair of extensions projecting radially away from the longitudinal axis; and
    a body member, the insert being rotatably disposed within the body member, the body member having a threaded portion disposed on an interior side wall of the body member, and a pair of opposed recesses disposed beneath the threaded portion, the pair of opposed recesses configured to receive the pair of extension, the pair of extensions working in concert with the pair of opposed recesses so as to only pivot the body member relative to the insert along an axis orthogonal to both the longitudinal axis and an axis defined by a line transverse to the pair of extensions.

9. The screw assembly of claim 8, wherein each of the extensions are diametrically opposed to each other and projecting radially away from the longitudinal axis and into the pair of opposed recesses of the body member.

10. The screw assembly of claim 8, wherein the head portion includes a cap having a diameter greater than a diameter of a proximal opening of the insert to prevent passage of the head portion distally through the insert and body member.

11. The screw assembly of claim 8, wherein the extensions include proximal surfaces that angle away from a plane that is normal to the longitudinal axis by a predetermined angle and are configured to limit pivoting of the body member to a predetermined pivot angle; and
    a distal surface that is curved and configured to permit pivoting of the body member.

* * * * *